United States Patent
Kim (10) Patent No.: US 7,401,003 B2
(45) Date of Patent: Jul. 15, 2008

(54) DIAGNOSIS METHOD AND APPARATUS FOR PERIPHERAL DEVICE OF HOST

(75) Inventor: Young-hye Kim, Gyeonggi-do (KR)

(73) Assignee: Samsung Electronics Co., Ltd., Suwon-Si (KR)

(*) Notice: Subject to any disclaimer, the term of this patent is extended or adjusted under 35 U.S.C. 154(b) by 1 day.

(21) Appl. No.: 10/183,045

(22) Filed: Jun. 27, 2002

(65) Prior Publication Data
US 2003/0149546 A1    Aug. 7, 2003

(30) Foreign Application Priority Data
Feb. 4, 2002    (KR) .............................. 2002-6199

(51) Int. Cl.
*G06F 11/00*    (2006.01)
(52) U.S. Cl. .................... 702/183; 702/183
(58) Field of Classification Search ............ 714/43–46; 702/183, 185–187
See application file for complete search history.

(56) References Cited

U.S. PATENT DOCUMENTS

| | | | | |
|---|---|---|---|---|
| 3,806,878 | A * | 4/1974 | Edstrom ...................... | 714/46 |
| 4,837,764 | A * | 6/1989 | Russello ..................... | 714/46 |
| 4,885,683 | A * | 12/1989 | Coogan ....................... | 714/36 |
| 4,964,124 | A * | 10/1990 | Burnett ........................ | 714/44 |
| 6,038,690 | A * | 3/2000 | Jacobson et al. .............. | 714/49 |
| 6,173,422 | B1 * | 1/2001 | Kimura et al. ................. | 714/57 |
| 6,347,335 | B1 * | 2/2002 | Shagam et al. ............... | 709/223 |
| 6,360,336 | B1 * | 3/2002 | Christensen et al. .......... | 714/47 |
| 6,385,739 | B1 * | 5/2002 | Barton et al. ................. | 714/25 |
| 6,430,711 | B1 * | 8/2002 | Sekizawa ..................... | 714/47 |
| 6,516,427 | B1 * | 2/2003 | Keyes et al. .................. | 714/25 |
| 6,532,547 | B1 * | 3/2003 | Wilcox ........................... | 714/5 |
| 6,578,167 | B2 * | 6/2003 | Boorom et al. ............... | 714/727 |
| 6,600,614 | B2 * | 7/2003 | Lenny et al. .................. | 360/31 |
| 6,710,893 | B1 * | 3/2004 | Hou et al. ..................... | 358/1.15 |
| 6,892,317 | B1 * | 5/2005 | Sampath et al. ................ | 714/4 |
| 2003/0193685 | A1 * | 10/2003 | Kageyama ................. | 358/1.14 |

FOREIGN PATENT DOCUMENTS

JP    55-112624    8/1980

(Continued)

OTHER PUBLICATIONS

U.S. Appl. No. 10/859,297, filed Jun. 3, 2004, Lee, Samsung Electronics Co., Ltd.

(Continued)

*Primary Examiner*—Edward Raymond
*Assistant Examiner*—Mohamed Charioui
(74) *Attorney, Agent, or Firm*—Staas & Halsey LLP (57) ABSTRACT

A diagnosis method for use with peripheral devices includes diagnosing states of the peripheral devices connected to a host, automatically and periodically, and outputting a history of diagnostic results to a predetermined storage unit. The diagnosis method further includes automatically stopping the diagnosis of the peripheral devices if the peripheral devices are operated by a user during the diagnosis, and resuming or restarting the diagnosis of the peripheral devices when the peripheral devices or the host return to idle. Consequently, a vendor of one of the peripheral devices may recognize the problems in the peripheral device, to efficiently manage the peripheral device while reducing cost for after-sale service.

43 Claims, 5 Drawing Sheets

FOREIGN PATENT DOCUMENTS

| | | | |
|---|---|---|---|
| JP | 63-108447 | | 5/1988 |
| JP | 5-35542 | | 2/1993 |
| JP | 7-13884 | | 1/1995 |
| JP | 09-160803 | | 6/1997 |
| JP | 09-160843 | | 6/1997 |
| JP | 09160843 A | * | 6/1997 |
| JP | 11-249924 | | 9/1999 |
| JP | 2002-014795 | | 1/2002 |
| KR | 1998-0011123 | | 4/1998 |
| KR | 2002-0065143 | | 8/2002 |

OTHER PUBLICATIONS

Korean Office Action issued on Dec. 23, 2004.

Japanese Office Action issued on Jun. 7, 2005, in Japanese Patent Application No.: 2002-315236 which corresponds to the U.S. Appl. No.: 10/183,045.

Japanese Office Action issued on Feb. 1, 2006, in Japanese Patent Application No.: 2002-315236 which corresponds to the U.S. Appl. No.: 10/183,045.

* cited by examiner

DIAGNOSIS METHOD AND APPARATUS FOR PERIPHERAL DEVICE OF HOST

CROSS-REFERENCE TO RELATED APPLICATION

This application claims the benefit of Korean Application No. 2002-6199, filed Feb. 4, 2002, in the Korean Intellectual Property Office, the disclosure of which is incorporated herein by reference.

BACKGROUND OF THE INVENTION

1. Field of the Invention

The present invention relates to a diagnosis method and apparatus for use with peripheral devices, and more particularly, to a method, apparatus, and medium for periodically diagnosing a host and the host's peripheral devices and storing a history of diagnostic results, and for transferring the history to the host or the vendor of the peripheral devices when troubles occur in the host or the peripheral devices.

2. Description of the Related Art

Generally, when peripheral devices of a host, such as a printer, scanner, or facsimile, are out of order, a user diagnoses the software or hardware of the host or the peripheral devices using a diagnosis program provided by the vendor of the host or the peripheral devices, or transfers diagnostic results to the vendor. The vendor receives the diagnostic results to diagnose the host or the peripheral devices based on the diagnostic results. However, the diagnostic results refer to the time that the troubles took place. Thus, the software and hardware states of the host or the peripheral devices before the troubles occur cannot be precisely diagnosed. In addition, if the troubles are fatal, the diagnosis program may not run, and the host or the peripheral devices cannot be diagnosed.

SUMMARY OF THE INVENTION

To solve the above and other problems, it is an object of the present invention to provide a method and apparatus for periodically diagnosing a host and peripheral devices thereof, storing the history of diagnostic results, and transferring the history to the host or the vendor of the peripheral devices when troubles take place.

Additional objects and advantages of the invention will be set forth in part in the description which follows and, in part, will be obvious from the description, or may be learned by practice of the invention.

To accomplish the above and other objects of the present invention, a diagnosis method for use with peripheral devices according to an embodiment of the invention comprises automatically and periodically diagnosing states of the peripheral devices connected to a host; and outputting a history of diagnostic results to a predetermined storage unit.

According to an aspect of the invention, the diagnosis method further includes automatically stopping the diagnosis of the peripheral devices if the peripheral devices are operated by a user during diagnosis; and resuming or restarting the diagnosis of the peripheral devices when the peripheral devices return to idle.

According to a further aspect of the invention, the diagnosis method further includes transferring the history to a customer management system of the peripheral device vendor; and diagnosing the peripheral devices and transferring diagnostic results to the storage unit when troubles occur while using the peripheral devices.

According to another aspect of the invention, the diagnosis interval is one of a default value set by a vendor of the peripheral device, and a value established and altered by the user.

According to another embodiment of the present invention, a diagnosis apparatus for use with peripheral devices comprises an automatic diagnosis unit to automatically and periodically diagnose states of the peripheral devices connected to a host, and to output diagnostic results; and a diagnostic result storage unit to receive the diagnostic results and to store a history of the diagnostic results.

According to a further aspect of the invention, if the peripheral devices are operated by a user while automatically diagnosing the states of the peripheral devices, the diagnosis is automatically stopped, and resumed or restarted when the peripheral devices return to idle.

According to another aspect of the invention, the automatic diagnosis apparatus transfers the history of the diagnostic results to a customer management system of a vendor of the peripheral device.

According to yet another aspect of the invention, if troubles occur while using the peripheral devices, the automatic diagnosis unit diagnoses the peripheral devices and outputs the diagnostic results to the diagnostic results storage unit.

According to still another aspect of the invention, the automatic diagnosis unit is a diagnosis program which automatically diagnoses the peripheral devices connected to the host and outputs the diagnostic results.

According to yet still another aspect of the invention, the diagnosis interval of the automatic diagnosis unit is determined as a default by the peripheral device vendor, or is established and altered by the user.

According an additional embodiment of the present invention, provided is a recording medium encoded with a program readable by a computer, the program implementing a method of operating a diagnosis process for peripheral devices of the computer, the method including automatically and periodically diagnosing states of the peripheral devices connected to a host; and outputting a history of diagnostic results to a predetermined recording apparatus.

According to an aspect of the invention, the method further includes automatically stopping the diagnosis of the peripheral devices if the peripheral devices are operated by a user during the diagnosis; and resuming or restarting the diagnosis of the peripheral devices when the peripheral devices return to idle.

BRIEF DESCRIPTION OF THE DRAWINGS

The above and other objects and advantages of the present invention will become more apparent and more readily appreciated by describing in detail embodiments thereof with reference to the accompanying drawings in which.

DETAILED DESCRIPTION OF THE EMBODIMENTS

The present invention will now be described more fully with reference to the accompanying drawings, in which embodiments of the invention are shown. Like reference numerals refer to like elements throughout the drawings. The embodiments are described below in order to explain the present invention by referring to the figures.

Figure 1:
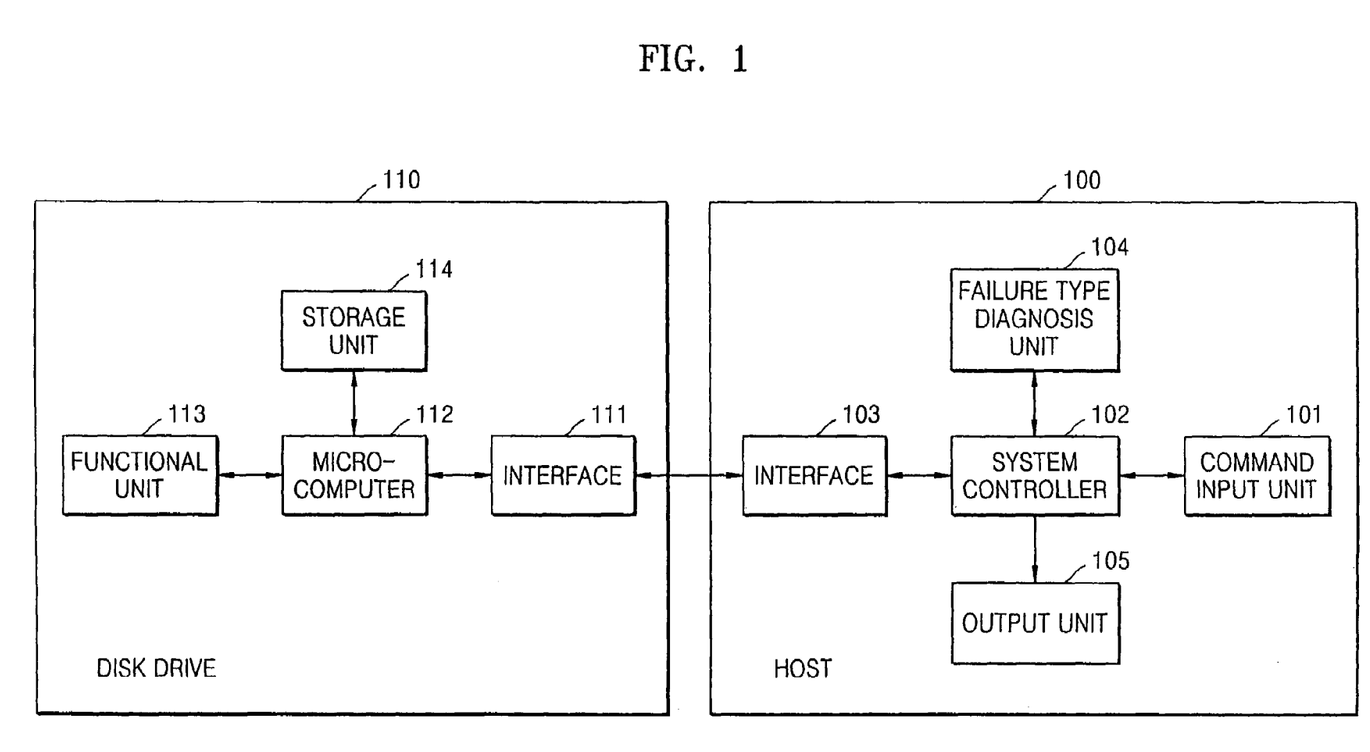
FIG. 1 is a flowchart depicting a diagnosis method for use with a peripheral device of a host according to an embodiment of the present invention.
Figure 2:
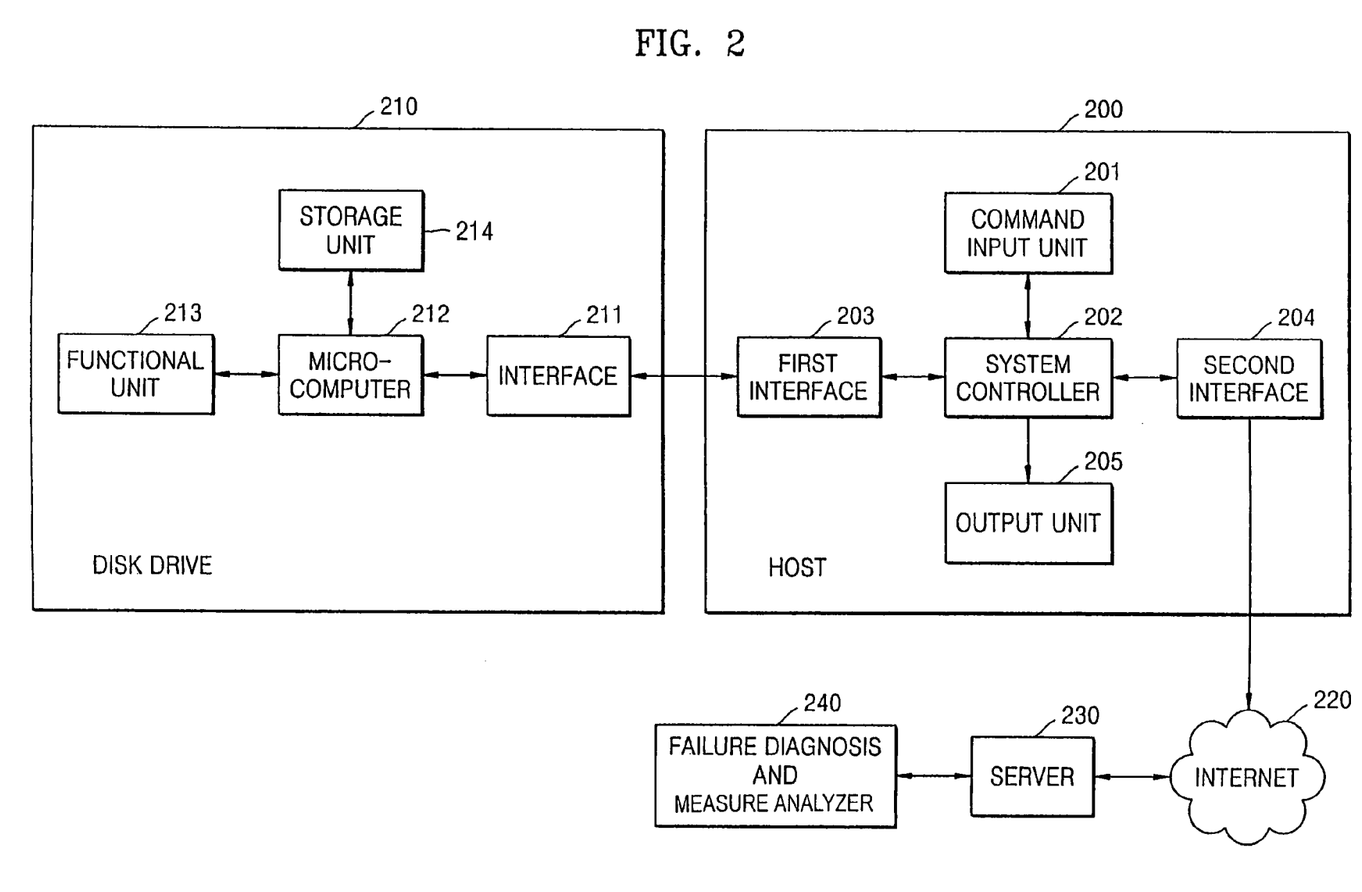
FIG. 2 is a block diagram depicting a diagnosis system for the peripheral devices of the host according to an embodiment of the present invention.
Figure 3:
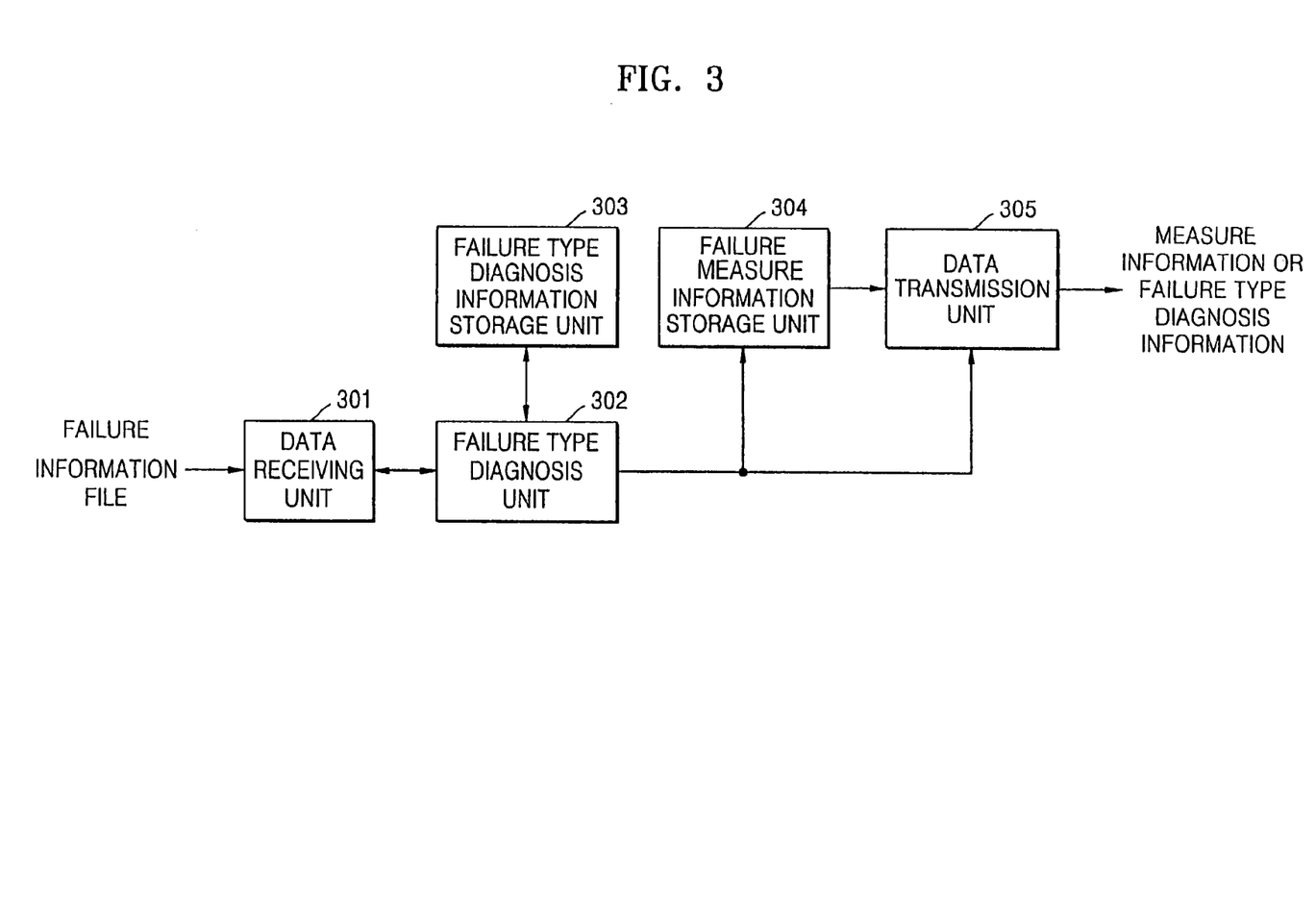
Figure 4:
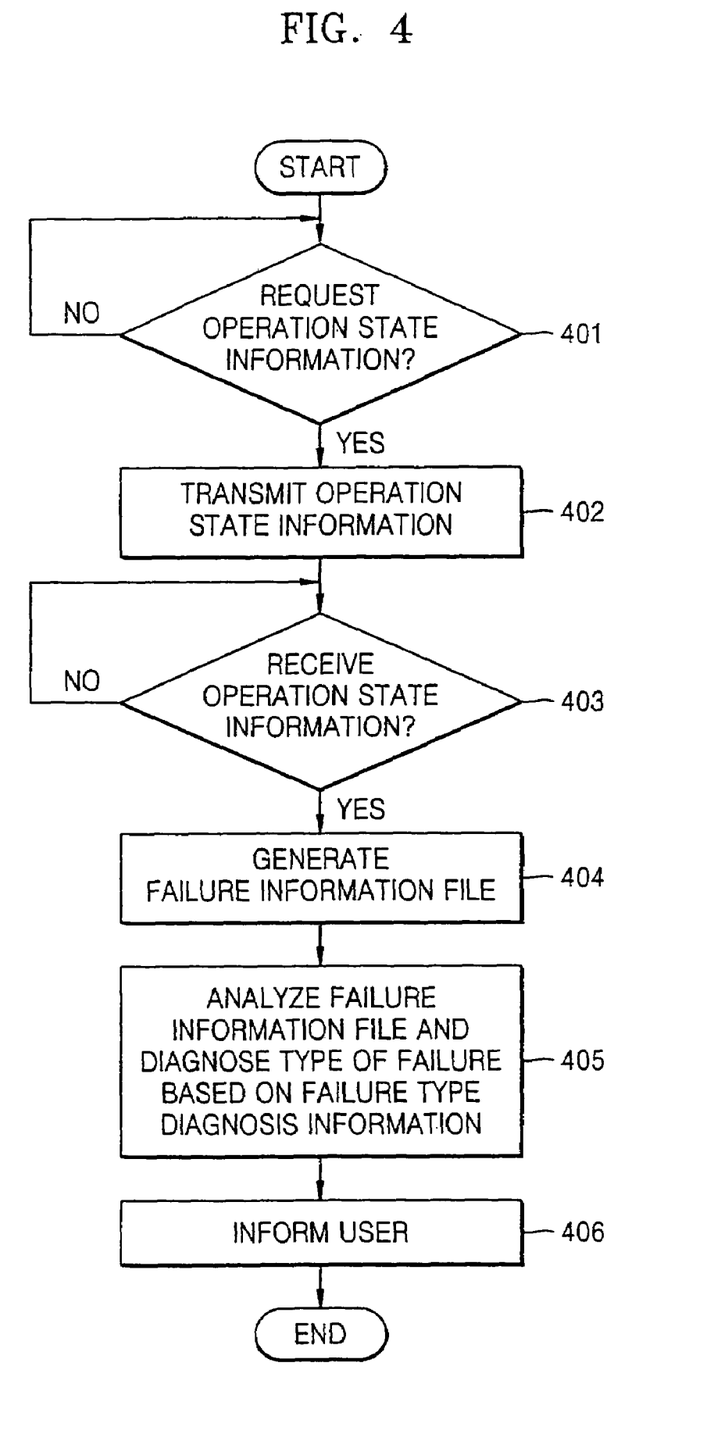
Figure 5:
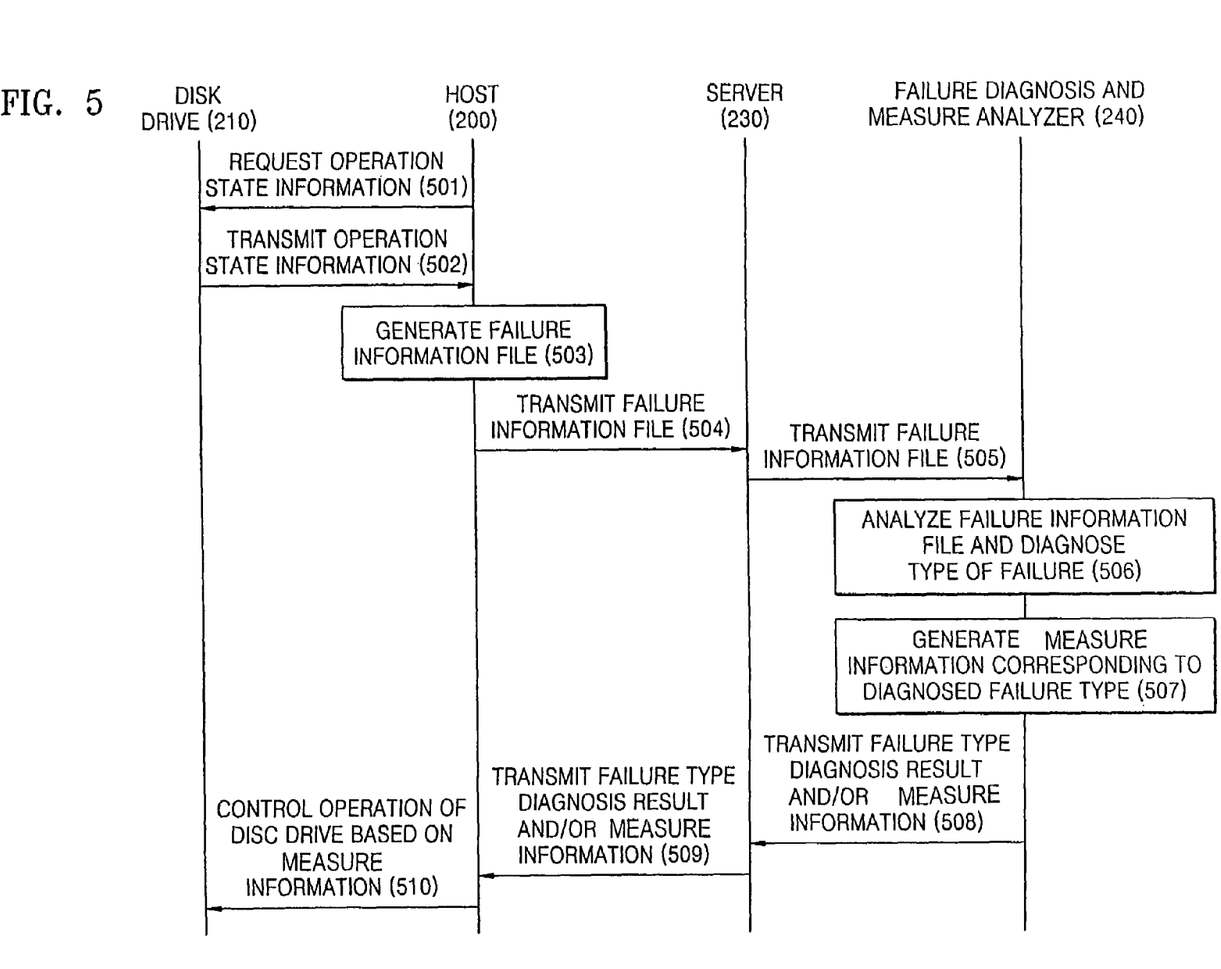

FIG. 1 is a flowchart depicting a diagnosis method for a peripheral device of a host according to an embodiment of the present invention. FIG. 2 is a block diagram depicting a diagnosis system for the peripheral devices of the host according to an embodiment of the present invention.

Referring to FIGS. 1 and 2, the diagnosis system comprises a host 100, such as a computer, having a diagnostic result storage unit 110 and an automatic diagnosis unit 120. Peripheral devices 130, 140 and a customer management system 150 of a peripheral device vendor are in communication with the host 100. According to an embodiment of the invention, the peripheral devices 130, 140 include a printer, a scanner, and a facsimile connected to the host 100 via a cable or wireless network. The host 100 and the customer management system 150 of the peripheral device vendor are connected via a cable or wireless network 160. However, it is understood that the peripheral devices could include home electronics, appliances, personal digital assistants (PDAs), and other items connectable to a computer. Further, it is understood that the diagnostic result storage unit 110 need not be part of the host 100 as shown in FIG. 2.

The automatic diagnosis unit 120 can be in the form of an apparatus, a diagnosis program, or a program driving apparatus according to embodiments of the invention. The automatic diagnosis unit 120 automatically operates at predetermined diagnosis intervals to diagnose, in detail, the software or hardware states of the peripheral devices 130, 140 connected to the host 100. Consequently, the automatic diagnosis unit 120 according to embodiments of the present invention is realized in software, hardware, or a combination thereof.

In addition, according to an embodiment of the invention, the automatic diagnosis unit 120 comprises a recording medium encoded with instructions readable by a computer, or hardware operated in connection with the instructions encoded on the recording medium. In these embodiments, the recording medium contains a program used to perform a diagnosis process, the process including automatically diagnosing the peripheral devices 130, 140 of the host 100 at the predetermined intervals, and transferring a history of diagnostic results to a predetermined diagnostic result storage unit 110 of the host 100.

The automatic diagnosis unit 120 periodically diagnoses the peripheral devices 130, 140 and periodically outputs the diagnostic results to the diagnostic result storage unit 110. According to embodiments of the invention, the diagnostic result storage unit 110 is either a removable or a fixed disk. A diagnosis interval of the automatic diagnosis unit 120 is determined as a default by the vendors of the peripheral devices. However, the interval is also established and altered by the user according to an embodiment of the invention. Using the user or the default diagnosis intervals, a schedule is established. The automatic diagnosis unit 120 diagnoses the peripheral devices 130, 140 according to the schedule.

Although the automatic diagnosis unit 120 follows the diagnosis intervals to diagnose the peripheral devices 130, 140, the automatic diagnosis unit 120 starts the diagnosis only when the peripheral devices 130, 140 are idle. If the peripheral devices 130, 140 are used while the automatic diagnosis unit 120 is operating, the automatic diagnosis unit 120 automatically stops and waits until the peripheral devices 130, 140 return to idle. Then, the automatic diagnosis unit 120 automatically resumes or restarts the diagnosis of the peripheral devices 130, 140. Thus, the automatic diagnosis unit 120 periodically diagnoses the software and hardware states of the peripheral devices 130, 140 connected to the host 100 at the intervals predetermined as a default by the vendor of the peripheral devices or the intervals established by the user (operation 10). The diagnostic result is stored in the diagnostic result storage unit 110. It is understood that, where only one of the peripheral devices 130, 140 is being accessed, the diagnosis can be continued for any of the peripheral devices 130, 140 not being accessed.

Similarly, if the user manually operates the automatic diagnosis unit 120 due to troubles occurring while using the peripheral devices 130, 140 of the host 100, the automatic diagnosis unit 120 transfers the diagnostic results to the diagnostic result storage unit 110. Accordingly, the states of the peripheral devices 130, 140 diagnosed automatically or manually by the automatic diagnosis unit 120 are transferred to the diagnostic result storage unit 110. The diagnostic result storage unit 110 stores the diagnostic results transferred from the automatic diagnosis unit 120 according to the order or time of the diagnosis (operation 20). Consequently, the diagnostic result storage unit 110 stores the history of the diagnostic results for the host 100 and/or the peripheral devices 130, 140.

The results of the diagnosis manually performed by the automatic diagnosis unit 120 are added to the existing history of the diagnosis results. The history is referred to as data that stores changes in information on the state of the host 100 and/or the peripheral devices 130, 140 (i.e. the diagnostic results of the host 100 and/or the peripheral devices 130, 140). The history can be unique to one of the host 100 and the peripheral devices 130, 140, or can include all or some of the host 100 and the peripheral devices 130, 140.

The automatic diagnosis unit 120 determines the existence of troubles in the host 100 and/or the peripheral devices 130, 140 (operation 30). If no trouble takes place in the host 100 and/or the peripheral devices 130, 140, the automatic diagnosis unit 120 repeats operation 10.

If troubles do take place in the host 100 and/or the peripheral devices 130, 140, the automatic diagnosis unit 120 transfers the results to the customer management system 150 of the peripheral device vendor via the cable or wireless network 160 (operation 40). According to an embodiment of the invention, the user determines whether to transfer the diagnostic results.

According to an embodiment of the invention, whenever the automatic diagnosis unit 120 performs the diagnosis, the automatic diagnosis unit 120 automatically transfers the history stored in the diagnostic result storage unit 110 to the customer management system 150 of the peripheral device vendor via the cable or wireless network 160. The transfer is performed regardless of the existence of troubles in the host 100 and/or peripheral devices 130, 140. In another embodiment, the user determines whether and how to transfer the history. For instance, the user transfers the history to the customer management system 150 of the peripheral device vendor by e-mail according to an embodiment of the invention.

However received, the customer management system 150 of the peripheral device vendor manages the used state, remaining amount, and problems of the host 100 and/or the peripheral devices 130, 140 using the received history of the diagnostic results. Consequently, the peripheral device vendor may recognize the problems in the peripheral devices 130, 140, to efficiently manage the peripheral devices 130, 140 while reducing cost for after-sale service. While described in terms of a vendor, the customer management system 150 can be used by any entity responsible for the maintenance of one of the peripheral devices 130, 140 and/or the host 100. Such an entity includes a supplier, a customer service desk, and a system administrator for a network including one of the peripheral devices 130, 140 and/or the host 100.

While the diagnosis method and apparatus for the peripheral devices of the host have been particularly shown and described with reference to a embodiment thereof, the embodiment described above is merely illustrative and is not intended to limit the scope of the invention. It will be understood by those skilled in the art that various changes in form and details may be made therein without departing from the spirit and scope thereof as defined by the accompanying claims and equivalents thereof.

What is claimed is:

1. A diagnosis apparatus for use with a peripheral device of a host, the apparatus comprising:
    an automatic diagnosis unit external to the peripheral device and which automatically and periodically performs a diagnostic on the peripheral device at a diagnoses interval to diagnose a state of the peripheral device connected to the host, to determine an existence of trouble in the host and/or the peripheral device, and to output diagnostic results, wherein the diagnoses interval is user adjustable; and
    a diagnostic result storage unit to receive the diagnostic results and to store a diagnostic history of the diagnostic results,
    wherein, if the peripheral device is operated while said automatic diagnosis unit is automatically diagnosing the state of the peripheral device, said automatic diagnosis unit automatically stops the diagnosis, and resumes or restarts when the peripheral device returns to idle, and
    wherein said automatic diagnosis unit transfers the history of the diagnostic results to a customer management system of a vendor of the peripheral device.

2. The diagnosis apparatus of claim 1, wherein the automatic diagnosis unit includes the diagnostic for use with the peripheral device and automatically and periodically connects to the peripheral device to perform the diagnostic on the peripheral device to diagnose the state of the peripheral device connected to the host, and to output the diagnostic results.

3. The diagnosis apparatus of claim 2, wherein the automatic diagnosis unit includes a diagnosis program including the diagnostic for use with the peripheral device and automatically and periodically connects to the peripheral device to perform the diagnostic on the peripheral device to diagnose the state of the peripheral device connected to the host, and to output the diagnostic results.

4. The diagnosis apparatus of claim 3, wherein the diagnosis program in the automatic diagnosis unit further includes another diagnostic for use with another peripheral device which is external to the automatic diagnosis unit and automatically and periodically connects to the another peripheral device to perform the another diagnostic on the another peripheral device to diagnose a state of the another peripheral device connected to the host, and to output the diagnostic results.

5. The diagnosis apparatus of claim 3, wherein the diagnosis program in the automatic diagnosis unit further includes another diagnostic for use with the host and automatically and periodically performs the another diagnostic on the host to diagnose a state of the host, and to output the diagnostic results.

6. The diagnosis apparatus of claim 2, wherein the automatic diagnosis unit further includes another diagnostic for use with another peripheral device which is external to the automatic diagnosis unit and automatically and periodically connects to the another peripheral device to perform the another diagnostic on the another peripheral device to diagnose a state of the another peripheral device connected to the host, and to output the diagnostic results.

7. The diagnosis apparatus of claim 2, wherein the automatic diagnosis unit further includes another diagnostic for use with the host automatically and periodically performs the another diagnostic on the host to diagnose a state of the host, and to output the diagnostic results.

8. The diagnostic apparatus of claim 1, wherein said automatic diagnosis unit outputs the diagnostic history to a support system, and receives an analysis of the outputted diagnostic history from the support system.

9. The diagnostic apparatus of claim 8, wherein said automatic diagnosis unit outputs the diagnostic history to the support system at a command of a user.

10. The diagnostic apparatus of claim 8, wherein said automatic diagnosis unit detects a problem in the peripheral device, and outputs the diagnostic history to the support system when the problem is detected.

11. The diagnostic apparatus of claim 8, wherein said automatic diagnosis unit outputs the diagnostic history to the support system using electronic mail.

12. The diagnostic apparatus of claim 1, wherein said automatic diagnosis unit automatically and periodically diagnoses a state of the host in addition to the state of the peripheral device, and outputs the diagnostic results of the host to be stored in said diagnostic result storage unit to form a diagnostic history of the host.

13. The diagnostic apparatus of claim 12, wherein said automatic diagnosis unit outputs the diagnostic history of the host to a host support system, and receives an analysis of the outputted diagnostic history of the host from the host support system.

14. The diagnostic apparatus of claim 12, wherein said automatic diagnosis unit detects when one of the peripheral device and host is being accessed, and stops the diagnosis being performed on the one of the peripheral device and the host being accessed.

15. The diagnosis apparatus of claim 1, wherein, if troubles occur while using the peripheral device, said automatic diagnosis unit diagnoses the peripheral device and outputs the diagnostic results to said diagnostic result storage unit.

16. The diagnosis apparatus of claim 1, further comprising a computer, wherein said automatic diagnosis unit comprises a diagnosis program used by said computer to automatically diagnose the peripheral device connected to the host and to output the diagnostic results.

17. The diagnostic apparatus of claim 1, wherein:
    said automatic diagnosis unit receives a signal to diagnose the state of the peripheral device other than at the diagnoses intervals, and
    in response to receiving the signal to diagnose the state of the peripheral device received other than at the diagnoses intervals, said automatic diagnosis unit diagnoses the state of the peripheral device and outputs the diagnostic results to said diagnostic result storage unit to be included in the diagnostic history.

18. The diagnostic apparatus of claim 12, wherein said automatic diagnosis unit is included in the host.

19. A diagnosis method for use with peripheral devices of a host, the method comprising:
    using diagnostics stored in the host, automatically and periodically performing the diagnostics on the peripheral devices at a diagnosis interval to diagnose states of the peripheral devices connected to the host, wherein the diagnoses interval is user adjustable;

outputting diagnostic results to a predetermined storage unit to form a history of the diagnostic results;
automatically stopping the diagnosis of the peripheral devices if the peripheral devices are operated during said diagnosing the states of the peripheral devices; and
resuming or restarting the diagnosis of the peripheral devices when the peripheral devices return to idle;
determining an existence of trouble in the host and/or the peripheral devices; and
transferring the history to a customer management system of a vendor of one of the peripheral devices in which an error occurs.

20. The diagnosis method of claim 1, wherein at least one of the peripheral devices comprises a scanner, a facsimile, an appliance, or a personal digital assistant (PDA).

21. The diagnosis method of claim 20, wherein at least another one of the peripheral devices comprises a printer.

22. The diagnosis apparatus of claim 1, wherein the peripheral device comprises a scanner, a facsimile, an appliance, or a personal digital assistant (PDA).

23. The diagnosis apparatus of claim 22, wherein the automatic diagnosis unit further automatically and periodically performs another diagnostic on another peripheral device comprising a printer.

24. The diagnosis method of claim 1, wherein:
the host is connected to an automatic diagnosis unit not included in the peripheral devices and which includes diagnostics to perform on the peripheral devices, and
the automatically and periodically performing diagnostics comprises the host controlling the automatic diagnosis unit to connect to the peripheral devices in order to perform the diagnostics on the peripheral devices.

25. The diagnosis method of claim 24, further comprising diagnosing the peripheral devices using the automatic diagnosis unit and transferring the diagnostic results from the automatic diagnosis unit to the storage unit when troubles occur while using the peripheral devices.

26. The diagnosis method of claim 24, further comprising the automatic diagnosis unit:
performing diagnostics on the host to which the peripheral devices are connected to diagnose a state of the host in addition to the states of the peripheral devices connected to the host; and
outputting diagnostic results of the host to the predetermined storage unit to form a history of the diagnostic results.

27. The diagnosis method of claim 1, further comprising diagnosing the peripheral devices and transferring the diagnostic results to the storage unit when troubles occur while using the peripheral devices.

28. The diagnosis method of claim 1, wherein said automatically and periodically diagnosing the states comprises establishing at least one diagnosis interval at which the states are automatically diagnosed.

29. A recording medium encoded with a program readable by a computer, the program implementing a method of operating a diagnosis process for use with a peripheral device of a host, the method comprising:
using diagnostics stored in the host including the computer, automatically and periodically performing the diagnostics on the peripheral device at a diagnosis interval to diagnose states of the peripheral device connected to the host, wherein the diagnosis interval is user adjustable;
outputting diagnostic results to a predetermined recording apparatus to form a diagnostic history of the diagnostic results;
automatically storing the diagnosis of the peripheral device if the peripheral device is operated during the diagnosis;
resuming or restarting the diagnosis of the peripheral device when the peripheral device returns to idle;
determining an existence of trouble in the host and/or the peripheral device; and
transferring the history to a customer management system of a vendor of the peripheral device.

30. The recording medium of claim 29, wherein the method further comprises outputting the diagnostic history to a support system.

31. The recording medium of claim 29, wherein at least one of the peripheral devices comprises a scanner, a facsimile, an appliance, or a personal digital assistant (PDA).

32. The recording medium of claim 31, wherein at least another one of the peripheral devices comprises a printer.

33. The recording medium of claim 30, wherein said outputting the diagnostic history is performed automatically and periodically.

34. The recording medium of claim 30, wherein said outputting the diagnostic history is performed at a received command.

35. The recording medium of claim 30, wherein the method further comprises detecting a problem in the peripheral device, and said outputting the diagnostic history is performed when the problem is detected.

36. The recording medium of claim 30, wherein said outputting the diagnostic history comprises sending the diagnostic history to the support system using electronic mail.

37. A recording medium encoded with a program readable by a computer, the program implementing a method of operating a diagnosis process for use with a peripheral device of a host, the method comprising:
using the host to automatically and periodically perform diagnostics on the peripheral device at a diagnostic interval to diagnose states of the peripheral device connected to the host, wherein the diagnoses interval is user adjustable;
outputting diagnostic results to a predetermined recording apparatus to form a diagnostic history of the diagnostic results;
automatically and periodically diagnosing a state of the host in addition to the state of the peripheral device;
outputting the diagnostic results of the host to form a diagnostic history of the host;
detecting when one of the peripheral device and host is being accessed;
stopping said diagnosing of the one of the peripheral device and the host being accessed;
resuming or restarting the diagnosis of the one of the peripheral device and host device when the one of the peripheral device and the host returns to idle; and
determining an existence of trouble in the host and/or the peripheral device; and
transferring the history to a customer management system of a vendor of the peripheral device.

38. The recording medium of claim 37, wherein the method further comprises outputting the diagnostic history of the host to a host support system.

39. The recording medium of claim 38, wherein said outputting the diagnostic history of the host comprises one of:
automatically and periodically outputting the diagnostic history of the host to the host support system, and
outputting the diagnostic history of the host to the host support system when a problem in the host is detected.

40. The recording medium of claim 38, wherein said automatically and periodically diagnosing the state of the peripheral device is performed by the host.

41. A diagnosis method for use with peripheral devices of a host, the method comprising:

using the host to automatically and periodically perform diagnostics on the peripheral devices at a diagnosis interval to diagnose states of the peripheral devices connected to the host, wherein the diagnosis interval is user adjustable;

outputting diagnostic results to a predetermined storage unit to form a history of the diagnostic results;

automatically stopping the diagnosis of the peripheral devices if the peripheral devices are operated during said diagnosing the states of the peripheral devices; and resuming or restarting the diagnosis of the peripheral devices when the peripheral devices return to idle;

determining an existence of trouble in the host and/or the peripheral devices; and transferring the history to a customer management system of a vendor of one of the peripheral devices in which an error occurs.

42. A recording medium encoded with a program readable by a computer, the program implementing a method of operating a diagnosis process for use with a peripheral device of a host, the method comprising:

using the host to automatically and periodically perform diagnostics on the peripheral devices to diagnose states of the peripheral device connected to the host to diagnose the state of the peripheral device connected to the host;

outputting diagnostic results to a predetermined recording apparatus to form a diagnostic history of the diagnostic results;

automatically stopping the diagnosis of the peripheral device if the peripheral device is operated during the diagnosis;

resuming or restarting the diagnosis of the peripheral device when the peripheral device returns to idle;

determining an existence of trouble in the host and/or the peripheral device; and transferring the history to a customer management system of a vendor of the peripheral device.

43. A recording medium encoded with a program readable by a computer, the program implementing a method of operating a diagnosis process for use with a peripheral device of a host, the method comprising:

using the host to automatically and periodically perform diagnostics on the peripheral device to diagnose states of the peripheral device connected to the host;

outputting diagnostic results to a predetermined recording apparatus to form a diagnostic history of the diagnostic results;

automatically stopping the diagnosis of the peripheral device if the peripheral device is operated during the diagnosis;

resuming or restarting the diagnosis of the peripheral device when the peripheral device returns to idle; and detecting when one of the peripheral device and host is being accessed;

wherein the using the host to automatically and periodically diagnose the state of the peripheral device connected to the host comprises, at predetermined diagnosis intervals which are user adjustable, automatically and periodically diagnosing the state of the peripheral device, and the method further comprises:

receiving a signal to diagnose the state of the peripheral device received other than at the predetermined intervals; and in response to receiving the signal to diagnose the state of the peripheral device received other than at the predetermined diagnosis intervals, diagnosing the state of the peripheral device and outputting the diagnostic results to be included in the diagnostic history; and transferring the history to a customer management system of a vendor of the peripheral device.

* * * * *

UNITED STATES PATENT AND TRADEMARK OFFICE
CERTIFICATE OF CORRECTION

PATENT NO. : 7,401,003 B2
APPLICATION NO. : 10/183045
DATED : July 15, 2008
INVENTOR(S) : Young-hye Kim It is certified that error appears in the above-identified patent and that said Letters Patent is hereby corrected as shown below:

Column 5, Lines 17-18, change "diagnoses" to --diagnosis--.

Column 5, Line 21, change "diagnoses" to --diagnosis--.

Column 6, Lines 50-51, change "diagnoses" to --diagnosis--.

Column 6, Lines 53-54, change "diagnoses" to --diagnosis--.

Column 6, Line 58, change "claim 12," to --claim 1,--.

Column 6, Line 66, change "diagnoses" to --diagnosis--.

Column 7, Line 5, after "devices" delete "and".

Column 7, Line 47, change "claim 1," to --claim 19,--.

Column 7, Line 51, change "claim 1," to --claim 19,--.

Column 7, Line 53, change "one" to --two--.

Column 7, Line 53, change "interval" to --intervals--.

Column 8, Line 1, change "storing" to --stopping--.

Column 8, Line 37, change "diagnoses" to --diagnosis--.

Column 8, Line 52, after "idle;" delete "and".

Column 9, Line 15, after "devices;" delete "and".

Column 9, Line 31, change "host;" to --host, wherein the diagnosis interval is user adjustable;--.

UNITED STATES PATENT AND TRADEMARK OFFICE
CERTIFICATE OF CORRECTION

| | | |
|---|---|---|
| PATENT NO. | : 7,401,003 B2 | |
| APPLICATION NO. | : 10/183045 | |
| DATED | : July 15, 2008 | |
| INVENTOR(S) | : Young-hye Kim | |

It is certified that error appears in the above-identified patent and that said Letters Patent is hereby corrected as shown below:

Column 10, Lines 20-21, change "detecting when one of the peripheral device and host is being accessed;" to --determining an existence of trouble in the host and/or the peripheral device,--.

Column 10, Line 30, after "vals;" delete "and".

Signed and Sealed this

Eleventh Day of November, 2008

JON W. DUDAS
*Director of the United States Patent and Trademark Office*

UNITED STATES PATENT AND TRADEMARK OFFICE
CERTIFICATE OF CORRECTION

PATENT NO. : 7,401,003 B2  Page 1 of 1
APPLICATION NO. : 10/183045
DATED : July 15, 2008
INVENTOR(S) : Young-hye Kim It is certified that error appears in the above-identified patent and that said Letters Patent is hereby corrected as shown below:

Column 7, Line 13, change "claim 1" to --claim 19--.
Column 7, Line 25, change "claim 1" to --claim 19--.

Signed and Sealed this

Thirteenth Day of October, 2009

David J. Kappos
*Director of the United States Patent and Trademark Office*

UNITED STATES PATENT AND TRADEMARK OFFICE
CERTIFICATE OF CORRECTION

PATENT NO.        : 7,401,003 B2
APPLICATION NO.   : 10/183045
DATED             : July 15, 2008
INVENTOR(S)       : Young-hye Kim

It is certified that error appears in the above-identified patent and that said Letters Patent is hereby corrected as shown below:

The title page should be delete and substitute therefor the attached title page.

Drawings:
Delete Fig. 2 and substitute therefor Fig. 2 as shown on the attached page.

Signed and Sealed this

Ninth Day of February, 2010

David J. Kappos
*Director of the United States Patent and Trademark Office*

United States Patent
Kim (10) Patent No.: US 7,401,003 B2
(45) Date of Patent: Jul. 15, 2008

(54) DIAGNOSIS METHOD AND APPARATUS FOR PERIPHERAL DEVICE OF HOST

(75) Inventor: Young-hye Kim, Gyeonggi-do (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1 day.

(21) Appl. No.: 10/183,045

(22) Filed: Jun. 27, 2002

(65) Prior Publication Data
US 2003/0149546 A1 Aug. 7, 2003

(30) Foreign Application Priority Data
Feb. 4, 2002 (KR) ............................. 2002-6199

(51) Int. Cl.
*G06F 11/00* (2006.01)
(52) U.S. Cl. ................................ 702/183; 702/183
(58) Field of Classification Search ............ 714/43–46; 702/183, 185–187
See application file for complete search history.

(56) References Cited

U.S. PATENT DOCUMENTS

| | | | | |
|---|---|---|---|---|
| 3,806,878 | A | * | 4/1974 | Edstrom ...................... 714/46 |
| 4,837,764 | A | * | 6/1989 | Russello ...................... 714/46 |
| 4,885,683 | A | * | 12/1989 | Coogan ...................... 714/36 |
| 4,964,124 | A | * | 10/1990 | Burnett ...................... 714/44 |
| 6,038,690 | A | * | 3/2000 | Jacobson et al. ............ 714/49 |
| 6,173,422 | B1 | * | 1/2001 | Kimura et al. ............... 714/57 |
| 6,347,335 | B1 | * | 2/2002 | Shagam et al. ............. 709/223 |
| 6,360,336 | B1 | * | 3/2002 | Christensen et al. ........ 714/47 |
| 6,385,739 | B1 | * | 5/2002 | Barton et al. ............... 714/25 |
| 6,430,711 | B1 | * | 8/2002 | Sekizawa .................... 714/47 |
| 6,516,427 | B1 | * | 2/2003 | Keyes et al. ................. 714/25 |
| 6,532,547 | B1 | * | 3/2003 | Wilcox ......................... 714/5 |
| 6,578,167 | B2 | * | 6/2003 | Boorom et al. ............. 714/727 |
| 6,600,614 | B2 | * | 7/2003 | Lenny et al. ................. 360/31 |
| 6,710,893 | B1 | * | 3/2004 | Hou et al. ................... 358/1.15 |
| 6,892,317 | B1 | * | 5/2005 | Sampath et al. ............. 714/4 |
| 2003/0193685 | A1 | * | 10/2003 | Kageyama ................. 358/1.14 |

FOREIGN PATENT DOCUMENTS

JP 55-112624 8/1980

(Continued)

OTHER PUBLICATIONS

U.S. Appl. No. 10/859,297, filed Jun. 3, 2004, Lee, Samsung Electronics Co., Ltd.

(Continued)

*Primary Examiner*—Edward Raymond
*Assistant Examiner*—Mohamed Charioui
(74) *Attorney, Agent, or Firm*—Staas & Halsey LLP (57) ABSTRACT

A diagnosis method for use with peripheral devices includes diagnosing states of the peripheral devices connected to a host, automatically and periodically, and outputting a history of diagnostic results to a predetermined storage unit. The diagnosis method further includes automatically stopping the diagnosis of the peripheral devices if the peripheral devices are operated by a user during the diagnosis, and resuming or restarting the diagnosis of the peripheral devices when the peripheral devices or the host return to idle. Consequently, a vendor of one of the peripheral devices may recognize the problems in the peripheral device, to efficiently manage the peripheral device while reducing cost for after-sale service.

43 Claims, 5 Drawing Sheets

FIG. 1

FIG. 2